(12) United States Patent
Taguchi et al.

(10) Patent No.: US 11,744,858 B2
(45) Date of Patent: Sep. 5, 2023

(54) MEDICINE FOR TREATMENT AND/OR PREVENTION OF ISCHEMIC DISEASES, METHOD FOR IMPROVING ANGIOGENESIS-PROMOTING ACTIVITY OF CELLS, OR METHOD FOR PRODUCING MEDICINE

(71) Applicant: Foundation for Biomedical Research and Innovation at Kobe, Kobe (JP)

(72) Inventors: Akihiko Taguchi, Hyogo (JP); Kenichi Yamahara, Hyogo (JP); Yukiko Niino, Hyogo (JP)

(73) Assignee: Foundation for Biomedical Research and Innovation at Kobe, Kobe (JP)

( * ) Notice: Subject to any disclaimer, the term of this patent is extended or adjusted under 35 U.S.C. 154(b) by 63 days.

(21) Appl. No.: 15/558,999

(22) PCT Filed: Mar. 18, 2016

(86) PCT No.: PCT/JP2016/001599
§ 371 (c)(1),
(2) Date: Sep. 15, 2017

(87) PCT Pub. No.: WO2016/147675
PCT Pub. Date: Sep. 22, 2016

(65) Prior Publication Data
US 2018/0243338 A1    Aug. 30, 2018

(30) Foreign Application Priority Data

Mar. 18, 2015 (JP) .................................. 2015-055185
Jul. 15, 2015 (JP) .................................. 2015-140966

(51) Int. Cl.
*A61K 35/14*    (2015.01)
*A61P 9/10*    (2006.01)
(Continued)

(52) U.S. Cl.
CPC .............. *A61K 35/14* (2013.01); *A61K 35/28* (2013.01); *A61K 38/1709* (2013.01);
(Continued)

(58) Field of Classification Search
CPC ............ A61K 35/28; A61K 35/14; A61P 9/10
See application file for complete search history.

(56) References Cited

U.S. PATENT DOCUMENTS

2002/0159981 A1   10/2002   Peled et al.
2004/0228834 A1   11/2004   Isner et al.
(Continued)

FOREIGN PATENT DOCUMENTS

JP    2002-506008    2/2002
JP    2003-523166    8/2003
(Continued)

OTHER PUBLICATIONS

Taguchi et al. "Therapeutic Angiogenesis by Autologous Bone-Marrow Transplantation in a General Hospital Setting" Eur J Vasc Endovasc Surg 25, 276-278. (Year: 2003).*
(Continued)

*Primary Examiner* — Blaine Lankford
*Assistant Examiner* — Lauren K Van Buren
(74) *Attorney, Agent, or Firm* — Knobbe, Martens, Olson & Bear, LLP (57) ABSTRACT

The present invention provides a sufficiently effective medicine for treatment and/or prevention of ischemic diseases, without performing isolation of therapeutic cells or removal of deleterious cells from blood cells/hemocytes. The blood cells and/or the hemocytes are subjected to the action of a saccharide. The saccharide is a monosaccharide, a disaccharide, a trisaccharide, a polysaccharides, or a copolymer
(Continued)

containing a monosaccharide, a disaccharide, or a trisaccharide as a component. The saccharide is a copolymer of sucrose and epichlorohydrin.

2 Claims, 4 Drawing Sheets

(51) Int. Cl.

| | |
|---|---|
| A61K 35/28 | (2015.01) |
| A61K 45/00 | (2006.01) |
| A61K 38/48 | (2006.01) |
| A61K 38/22 | (2006.01) |
| A61K 38/46 | (2006.01) |
| A61P 13/12 | (2006.01) |
| A61K 38/17 | (2006.01) |
| A61K 38/18 | (2006.01) |
| C12N 5/00 | (2006.01) |

(52) U.S. Cl.
CPC ...... *A61K 38/1825* (2013.01); *A61K 38/1841* (2013.01); *A61K 38/1858* (2013.01); *A61K 38/1866* (2013.01); *A61K 38/22* (2013.01); *A61K 38/46* (2013.01); *A61K 38/48* (2013.01); *A61K 38/4886* (2013.01); *A61K 45/00* (2013.01); *A61P 9/10* (2018.01); *A61P 13/12* (2018.01); *C12N 5/0087* (2013.01); *C12Y 304/24024* (2013.01)

(56) References Cited

U.S. PATENT DOCUMENTS

| | | | | |
|---|---|---|---|---|
| 2009/0048358 | A1* | 2/2009 | Kim | ............. A61L 27/44 521/76 |
| 2011/0076770 | A1* | 3/2011 | Sakai | ............. C12N 5/0663 435/383 |
| 2012/0064043 | A1* | 3/2012 | Ferguson | ............. A61L 27/3604 424/93.7 |

FOREIGN PATENT DOCUMENTS

| | | | | |
|---|---|---|---|---|
| JP | 2007-175008 | | 7/2007 | |
| JP | 2007175008 | * | 7/2007 | |
| WO | WO-2006102933 A1 | * | 10/2006 | ............. A61K 35/28 |
| WO | WO-2014099198 A1 | * | 6/2014 | ............. A61K 35/15 |

OTHER PUBLICATIONS

Naung et al. "Comparative study of different centrifugation protocols for a density gradient separation media in isolation of osteoprogenitors from bone marrow aspirate" Journal of Oral Biology and Craniofacial Research 4(2014) 160-168 (Year: 2014).*
Taguchi et al. "Therapeutic Angiogenesis by Autologous Bone-marrow Transplantation in a General Hospital Setting" Eur J Vasc Endovasc Surg, 25, 276-278 (2003) (Year: 2003).*
Chopp et al., "Antibodies Against Adhesion Molecules Reduce Apoptosis After Transient Middle Cerebral Artery Occlusion in Rat Brain," Journal of Cerebral Blood Flow and Metabolism; Jul. 1996; vol. 16, No. 4; pp. 578-584.
Del Zoppo et al., "Polymorphonuclear Leukocytes Occlude Capillaries Following Middle Cerebral Artery Occlusion and Reperfusion in Baboons," Stroke; Oct. 1991; vol. 22, No. 10; pp. 1276-1283.
Kishino et al., "Isolation of Mononuclear Cells From Bone Marrow Blood for Bone Marrow Transplantation Using Sepax™," Japanese Journal of Transfusion and Cell Therapy; 2012; vol. 58, No. 3; pp. 456-462.
Kudo et al., "Autologous Transplantation of Peripheral Blood EndotheliAl Progenitor Cells (CD34Sup+) for Therapeutic Angiogenesis in Patients With Critical Limb Ischemia," International Angiology; Turin 22.4; Dec. 2003; pp. 344-348.
Lefer et al., "A Novel Sialyl Lewis$^x$ Analog Attenuates Neutrophil Accumulation and Myocardial Necrosis After Ischemia and Reperfusion," Circulation; Nov. 1994; vol. 90, No. 5; pp. 2390-2401.
Lin et al., "Autologous Transplantation of Bone Marrow Mononuclear Cells Improved Heart Function After Myocardial Infarction," Acta Pharmacol Sin; Jul. 2004; 25 (7); pp. 876-886.
Nakano-Doi et al., "Bone Marrow Mononuclear Cells Promote Proliferation of Endogenous Neural Stem Cells Through Vascular Niches After Cerebral Infarction," Stem Cells; Jul. 2010; 28(7); pp. 1292-1302.
Oda Masato, et al, "Establishment of Culturing System for Ex-Vivo Expansion of Angiogenic Immature Erythroid," Journal of Molecular and Cellular Cardiology; 2010; vol. 49; pp. 347-353.
Taguchi et al., "Administration of CD34+ Cells After Stroke Enhances Neurogenesis Via Angiogenesis in a Mouse Model," The Journal of Clinical Investigation; Aug. 2004; vol. 114, No. 3; pp. 330-338.
Taguchi et al., "Therapeutic Angiogenesis by Autologous Bone-Marrow Transplantation in a General Hospital Setting," EurJ Vasc Endovasc Surg.; Mar. 2003; 25(3):276-8.
Dulbecco, "Dulbecco's Modified Eagle Medium/ Nutrient Mixture F-12 Ham (DMEM/ F12, 1:1 Mixture) With 15mM HEPES buffer, L-Glutamine, Sodium bicarbonate and Trace elements Without Phenol red 1X Liquid Cell Culture Medium Product Code: AL187A Product Description".
Extended European Search Report received in European Patent Application No. 16764506.8 dated Mar. 15, 2018 in 10 pages.
Melanie Lavergne et al, "Porous Polysaccharide-Based Scaffolds for Human Endothelial Progenitor Cells", Macromolecular Bioscience, DE, (Jun. 13, 2012), vol. 12, No. 7, doi:10.1002/mabi.201100431, ISSN 1616-5187, pp. 901-910.
Jun Hee Lee et al, "The Sulfated Polysaccharide Fucoidan Rescues Senescence of Endothelial Colony-Forming Cells for Ischemic Repair: Role of Fucoidan in ECFC Senescence Rescue", Stem Cells., US, (Feb. 19, 2015), vol. 33, No. 6, doi:10.1002/stem.1973, ISSN 1066-5099, pp. 1939-1951.
G. Sarlon et al, "Therapeutic effect of fucoidan-stimulated endothelial colony-forming cells in peripheral ischemia : Proangiogenic role of fucoidan in vivo", Journal of Thrombosis and Haemostasis, GB, (Jan. 1, 2012, vol. 10, No. 1, doi:10.1111/j.1538-7836.2011.04554.x, ISSN 1538-7933, pp. 38-48.
May-Jywan Tsai et al, "Recovery of neurological function of ischemic stroke by application of conditioned medium of bone marrow mesenchymal stem cells derived from normal and cerebral ischemia rats", Journal of Biomedical Science, Kluwer Academic Publishers, DO, (Jan. 22, 2014), vol. 21, No. 1, doi: 10.1186/1423-0127-21-5, ISSN 1423-0127, p. 5.
Xu et al, "Human bone marrow mesenchymal stem cell transplantation attenuates axonal injury in stroke rats", Neural Regeneration Research, CN, (Jan. 1, 2014), vol. 9, No. 23, doi:10.4103/1673-5374.147930, ISSN 1673-5374, p. 2053.
Kishino et al., "Isolation of Mononuclear Cells from Bone Marrow Blood for Bone Marrow Transplantation Using Sepax™," Japanese Journal of Transfusion and Cell Therapy Journal; 2012; vol. 58; No. 3; pp. 456-462.
Hernandez et al; Autologous bone-marrow mononuclear cell implantation in patients with severe lower limb ischaemia: A comparison of using blood cell separator and Ficoil density gradient centrifugation, Atherosclerosis, vol. 194, No. 2, pp. e52-e56, dated Oct. 6, 2007.
Marina Radrizzani et al; Bone marrow-derived cells for cardiovascular cell therapy: an optimized GMP method based on low-density gradient improves cell purity and function; Journal of Translational Medicine; vol. 12, No. 1, p. 276, dated Sep. 27, 2014.
Communication pursuant to Article 94(3) EPC, issued in Application No. 16764506.8, dated Oct. 14, 2021.
Seeger et al., "Cell isolation procedures matter: a comparison of different isolation protocols of bone marrow mononuclear cells used for cell therapy in patients with acute myocardial infarction", European Heart Journal, vol. 28, No. 6, pp. 766-772 (2007).

* cited by examiner

Atrophy index = X/Y x100 %

MEDICINE FOR TREATMENT AND/OR PREVENTION OF ISCHEMIC DISEASES, METHOD FOR IMPROVING ANGIOGENESIS-PROMOTING ACTIVITY OF CELLS, OR METHOD FOR PRODUCING MEDICINE

CROSS-REFERENCE TO RELATED APPLICATIONS

This application is the U.S. National Phase under 35. U.S.C. § 371 of International Application PCT/JP2016/001599, filed Mar. 18, 2016, which claims priority to Japanese Patent Application No. 2015-055185, filed Mar. 18, 2015 and Japanese Patent Application No. 2015-140966, filed Jul. 15, 2015. The disclosures of the above-described applications are hereby incorporated by reference in their entirety.

TECHNICAL FIELD

The present invention relates to a medicine for treatment and/or prevention of an ischemic disease, a method for improving angiogenesis-promoting activity of cells, or a method for producing such a medicine for treatment and/or prevention of an ischemic disease.

BACKGROUND ART

An ischemic disease refers to ischemia of an organ caused by occlusion or stenosis of an artery via which the organ obtains nutrition, and involves necrosis or dysfunction of a tissue of the organ resulting from oxygen deficiency or undernourishment. The ischemic diseases include various types of diseases such as myocardial infarction, limb ischemia, cerebral infarction, renal infarction, pulmonary infarction, splenic infarction, and bowel infarction.

For the functional recovery of a tissue damaged by the ischemic disease, it is important to protect/activate an associated microvascular network. In recent years, cell transplantation has been found to be effective in enhancing such functional recovery. Non-Patent Document 1 describes that as a treatment of myocardial infarction, administration of bone marrow mononuclear cells obtained by specific gravity centrifugation increases the vascular density of a microvascular network of the heart and improves the heart function. Non-Patent Document 2 describes that as a treatment of limb ischemia, administration of peripheral blood-derived CD34(+) cells purified using a specific cell surface antigen increases the vascular density of a microvascular network of the limbs and improves the ischemic symptoms. Non-Patent Document 3 describes that as a treatment of limb infarction, administration of bone marrow mononuclear cells obtained by specific gravity centrifugation increases the vascular density of a microvascular network of the limbs and improves the ischemic symptoms. Non-Patent Document 4 describes that as a treatment of cerebral infarction, administration of cord blood-derived CD34(+) cells purified using a specific cell surface antigen increases the vascular density of a microvascular network of the brain and improves the neural function. Non-Patent Document 5 describes that as a treatment of cerebral infarction, administration of bone marrow mononuclear cells obtained by specific gravity centrifugation increases the vascular density of a microvascular network of the brain and improves the neural function.

In this regard, however, it is known that cord blood, peripheral blood, and bone marrow each contain various types of cells including ones which aggravate the ischemic symptoms and worsen functional prognosis. Non-Patent Document 6 describes that polymorphonuclear leukocytes induce damage to a microvascular network and aggravate symptoms after myocardial infarction. Non-Patent Document 7 describes that polymorphonuclear leukocytes induce damage to a microvascular network and aggravate symptoms after cerebral infarction. Non-Patent Document 8 describes that adhering of neutrophilic leukocytes to a microvascular network aggravates cerebral infarction symptoms.

As can be seen from the foregoing, cells existing in cord blood, peripheral blood, and bone marrow include therapeutic cells which are effective in treating damage to microvascular networks/organs after ischemia and cells which aggravate the damage to microvascular networks/organs. Therefore, isolation of the therapeutic cells or removal of the deleterious cells are considered to be important for cell transplantation to have therapeutic effects. For example, the isolation of cells may be carried out using cell surface antigens, and isolation of mononuclear cells may be performed by removal of polymorphonuclear leucocytes/neutrophilic leukocytes through the specific gravity centrifugation.

CITATION LIST

Non-Patent Documents

NON-PATENT DOCUMENT 1: Autologous transplantation of bone marrow mononuclear cells improved heart function after myocardial infarction. Lin et al. Acta Pharmacol Sin 2004 July; 25 (7): 876-886

NON-PATENT DOCUMENT 2: Autologous transplantation of peripheral blood endothelial progenitor cells (CD34+) for therapeutic angiogenesis in patients with critical limb ischemia. Kudo et al. Int Angiol. 2003 December; 22(4):344-8.

NON-PATENT DOCUMENT 3: Therapeutic Angiogenesis by Autologous Bone-marrow Transplantation in a General Hospital Setting. Taguchi et al. Eur J Vasc Endovasc Surg. 2003 March; 25(3): 276-8.

NON-PATENT DOCUMENT 4: Administration of CD34+ cells after stroke enhances neurogenesis via angiogenesis in a mouse model. Taguchi et al. J Clin Invest. 2004 August; 114(3): 330-8.

NON-PATENT DOCUMENT 5: Bone marrow mononuclear cells promote proliferation of endogenous neural stem cells through vascular niches after cerebral infarction. Nakano-Doi et al. Stem Cells. 2010 July; 28(7): 1292-302.

NON-PATENT DOCUMENT 6: A novel sialyl LewisX analog attenuates neutrophil accumulation and myocardial necrosis after ischemia and reperfusion. Lefer et al. Circulation. 1994 November; 90(5): 2390-401

NON-PATENT DOCUMENT 7: Polymorphonuclear leukocytes occlude capillaries following middle cerebral artery occlusion and reperfusion in baboons. del Zoppo et al. Stroke. 1991 October; 22(10): 1276-83.

NON-PATENT DOCUMENT 8: Antibodies against adhesion molecules reduce apoptosis after transient middle cerebral artery occlusion in rat brain Chopp et al. J Cereb Blood Flow Metab. 1996 July; 16(4): 578-84.

SUMMARY OF THE INVENTION

Technical Problem

Unfortunately, the removal of polymorphonuclear leucocyte/neutrophilic leukocytes by the specific gravity centrifugation requires an expensive blood cell component separator or complicated operation using a gravity separation medium. Furthermore, it is known that a target cell fractionation is not always recovered at a high recovery rate through the isolation of cells using cell surface antigens or the removal of polymorphonuclear leucocyte/neutrophilic leukocytes by the specific gravity centrifugation.

In view of the above-described problems, it is therefore an object of the present invention to provide a sufficiently effective medicine for treatment and/or prevention of an ischemic disease, without performing isolation of therapeutic cells or removal of deleterious cells from blood cells/hemocytes containing various types of cells. Another object of the present invention is to provide a novel method for improving angiogenesis-promoting activity of cells. Yet another object of the present invention is to provide a novel method for producing a medicine for treatment and/or prevention of an ischemic disease.

Solution to the Problem

A medicine according to the present invention is for treatment and/or prevention of an ischemic disease and includes blood cells and/or hemocytes. The blood cells and/or the hemocytes have been subjected to an action of a saccharide. The saccharide is a monosaccharide, a disaccharide, a trisaccharide, a polysaccharide, or a copolymer containing a monosaccharide, a disaccharide or a trisaccharide as a component. According to the present invention, a method for improving angiogenesis-promoting activity of cells includes subjecting blood cells and/or hemocytes to an action of a saccharide. The saccharide is a monosaccharide, a disaccharide, a trisaccharide, a polysaccharide, or a copolymer containing a monosaccharide, a disaccharide or a trisaccharide as a component. According to the present invention, a method for producing a medicine for treatment and/or prevention of an ischemic disease includes subjecting blood cells and/or hemocytes to an action of a saccharide. The saccharide is a monosaccharide, a disaccharide, a trisaccharide, a polysaccharide, or a copolymer containing a monosaccharide, a disaccharide or a trisaccharide as a component.

Advantages of the Invention

The present invention may provide a sufficiently effective medicine for treatment and/or prevention of an ischemic disease, without performing isolation of therapeutic cells or removal of deleterious cells from blood cells/hemocytes containing various types of cells.

BRIEF DESCRIPTION OF THE DRAWINGS

FIGS. 1A, 1B and 1C show revascularization effects achieved by administration of bone marrow cells.

FIGS. 2A and 2B show vascular protection effects achieved by administration of bone marrow cells.

DESCRIPTION OF EMBODIMENTS

Embodiments of the present invention will now be described specifically with reference to the attached drawings. Note that the following embodiments are described for better understanding of the principles of the present invention, and that the scope of the present invention is not limited to the following embodiments. Other embodiments corresponding to the following embodiments of which a conFIGuration is appropriately replaced by the skilled person are also included in the scope of the present invention.

The inventors of the present invention have made surprising findings: subjecting a blood cell group and/or a hemocyte group to an action of a saccharide makes the blood cell group and/or the hemocyte group sufficiently effective in treating an ischemic disease, and eliminates need for isolation of therapeutic cells or removal of deleterious cells, despite the fact that the blood cell group and/or the hemocyte group is/are considered to contain various types of cells. The present invention has been made based on the findings. Subjecting the blood cells and/or the hemocytes to an action of a saccharide means adding the saccharide to a cell suspension of the blood cells and/or the hemocytes, thereby bringing the saccharide into contact with the blood cells and/or the hemocytes.

As will be shown in the examples described later, the present inventors induce a cellular function of treating ischemic diseases by adding a copolymer including sucrose as a component or maltose to a cell suspension. On a cell membrane, membrane domains exist which are rich in glycolipid and glycoprotein, and allow co-localization of various adhesion molecules, receptor molecules, and intracellular signaling molecules. Although not wishing to be bound by this theory, it is presumed that an interaction between a saccharide and glycolipid or other substances existing on a cell membrane induces the cellular function of treating the ischemic diseases.

Applicable examples of the saccharide include a wide range of saccharides, such as monosaccharides, disaccharides, trisaccharides, a polysaccharides, and a copolymer containing a monosaccharide, a disaccharide or a trisaccharide as a component. Examples of the monosaccharides include glucose, galactose, mannose, and fructose. Examples of the disaccharides include maltose, lactose, and sucrose. Examples of the trisaccharides include nigerotriose, maltotriose, and melezitose. Examples of the polysaccharides include starch, cellulose, and glycogen. Examples of the copolymer include a copolymer containing sucrose as a component, preferably a copolymer of sucrose and epichlorohydrin, more preferably FICOLL PM70 or FICOLL PM400, and most preferably FICOLL PM400. Note that in the present invention, it is beneficial not to subject blood cells and/or hemocytes to the action of sodium diatrizoate.

The blood cells and/or the hemocytes are preferably peripheral blood cells, bone marrow cells, or cord blood cells. The peripheral blood cells refer to cells existing in peripheral blood, such as leukocytes, erythrocytes, thrombocytes, and other cells. The bone marrow cells collectively refer to hematopoietic cells contained in bone marrow in a bone, and include leukocytic cells such as myeloblasts, erythroblast cells, bone marrow megakaryocytes, plasmacytes, and other cells. The cord blood cells broadly refer to cells extracted from an umbilical cord. The peripheral blood cells, which contain less hematopoietic stem cells and similar cells than the bone marrow cells, are considered to be unfit for cellular therapy. However, according to the present invention, the peripheral blood cells are made effective in treating the ischemic diseases simply by subjecting the peripheral blood cells to the action of a saccharide, without using a hematopoietic factor such as G-CSF, as will be shown in Example 5 later.

The medicine of the present invention is for treatment and/or prevention of ischemic diseases. In this respect, "treatment" as used herein includes treating symptoms, improving symptoms, and slowing the progression of symptoms. "Prevention" as used herein includes preventing and slowing the onset of the diseases, and refers to not only prevention before the onset of the diseases, but also prevention of the recurrence of the diseases after treatment.

The medicine of the present invention is for the ischemic diseases including, for example, cerebral infarction, myocardial infarction, limb ischemia, renal infarction, pulmonary infarction, splenic infarction, and bowel infarction. As will be shown in examples later, according to the present invention, blood cells and/or hemocytes subjected to the action of a saccharide are used to increase the microvascular density in a surrounding area of an ischemic region, thereby curing the ischemic diseases. The diseases which the present invention is intended to treat and prevent are not limited to those described in the examples.

The medicine of the present invention may be used in all of a hyperacute phase, an acute phase, a subacute phase, and a chronic phase. In particular, the medicine of the present invention may be preferably used in the acute and subacute phases of acute onset ischemic diseases such as acute myocardial infarction and acute cerebral infarction. Here, the hyperacute phase refers to a phase within 12 hours from the onset. In the hyperacute phase, it is probable that treatments such as stenting, thrombolytic therapy, and thrombectomy can prevent tissue cell death. The acute phase refers to a phase of from 12 hours to 7 days after the onset. The subacute phase refers to a phase of from 1 week to 4 weeks after the onset. The chronic phase refers to a phase of from 1 month after the onset. On the other hand, the medicine of the present invention may be preferably used irrespective of the phases, for chronically progressive ischemic diseases such as limb ischemia due to chronic circulatory disturbance. Beneficial examples of route of administration include intravenous administration, intra-arterial administration, intraportal administration, and local tissue administration.

The number of cells to be administered is not limited to a particular number. For example, in the case of intravenous administration, the number of cells may range from $1 \times 10^5$ cells/kg to $1 \times 0^9$ cells/kg, preferably from $1 \times 10^6$ cells/kg to $1 \times 10^8$ cells/kg, and more preferably $1 \times 10^7$ cells/kg.

The period during which a saccharide added to a cell suspension of blood cells and/or hemocytes is kept in contact with the blood cells and/or the hemocytes varies depending on the concentration of the saccharide and the type and number of cells to be administered, and is not limited to a particular period. For example, the period is from 5 minutes to 1 hour, preferably from 10 minutes to 30 minutes, more preferably 15 minutes to 25 minutes and most preferably 20 minutes.

The medicine of the present invention may further include a revascularization promoting factor. Non-limiting examples of the revascularization promoting factor include VEGF, angiopoietin, PDGF, TGF-β, FGF, P1GF, matrix metalloprotease, and plasminogen activator. Among these, the angiopoietins are preferably used as the revascularization promoting factors. The angiopoietins are glycoprotein growth factors promoting vasculogenesis or angiogenesis. There are four angiopoietins, namely, angiopoietin-1 (Ang1), angiopoietin-2 (Ang2), angiopoietin-3 (Ang3), and angiopoietin-4 (Ang4). In addition, there are six proteins similar to the angiopoietins, i.e., angiopoietin-related proteins (ANGPTLs) or angiopoietin-like proteins.

If the medicine of the present invention is prepared as an injectable preparation, any additives employed in the related technical field may be appropriately used. Examples of the additives include isotonic agents, stabilizers, buffers, preservatives, chelators, antioxidants, and solubilizers. Examples of the isotonic agents include saccharides such as glucose, sorbitol, and mannitol, sodium chloride, glycerine, propylene glycol, and polyethylene glycol. Examples of the stabilizers include sodium sulfite. Examples of the buffers include borate buffers, phosphate buffers, citrate buffers, tartrate buffers, and acetate buffers. Examples of the preservatives include p-hydroxybenzoate ester, benzyl alcohol, chlorocresol, phenethyl alcohol, and benzethonium chloride. Examples of the chelators include edetate sodium and sodium citrate. Examples of the antioxidants include sodium sulfite, sodium hydrogen sulfite, sodium ascorbate, and sodium thiosulfate. Examples of the solubilizers include dextran, polyvinyl pyrrolidone, sodium benzoate, ethylenediamine, salicylamide, nicotinamide, and polyoxyethylene-setting castor oil derivatives.

According to the present invention, a method for improving angiogenesis-promoting activity of cells includes subjecting blood cells and/or hemocytes to an action of a saccharide. The saccharide is a monosaccharide, a disaccharide, a trisaccharide, a polysaccharide, or a copolymer containing a monosaccharide, a disaccharide or a trisaccharide as a component.

According to the present invention, a method for producing a medicine for treatment and/or prevention of an ischemic disease includes subjecting blood cells and/or hemocytes to an action of a saccharide. The saccharide is a monosaccharide, a disaccharide, a trisaccharide, a polysaccharide, or a copolymer containing a monosaccharide, a disaccharide or a trisaccharide as a component.

If the blood cells and/or the hemocytes are bone marrow cells, it is beneficial to subject, to the action of FICOLL PM400, a bone marrow cell suspension obtained by removing an erythrocyte fraction from a bone marrow fluid using, for example, hydroxyethyl starch. In this case, the cells are caused to have therapeutic effect on the ischemic diseases without selecting a leukocyte fraction. Thus, despite the simplicity of the process, the present invention is capable of imparting function of curing ischemia to the cells.

If the blood cells and/or the hemocytes are peripheral blood cells, it is beneficial to subject, to the action of FICOLL PM400, a buffy coat layer which is the middle layer of three separated layers obtained by centrifuging peripheral blood using, for example, FICOLL-Paque.

Like the medicine for treatment and/or prevention of ischemic diseases according to the present invention, a wide range of saccharides is applicable to the method for improving angiogenesis-promoting activity of cells and the method for producing a medicine for treatment and/or prevention of an ischemic disease according to the present invention. Examples of applicable saccharides include maltose and a copolymer of sucrose and epichlorohydrin.

EXAMPLES

Example 1

Revascularization and vascular protection effects achieved by bone marrow cells subjected to the action of a sugar chain polymer FICOLL PM400 is a copolymer of sucrose and epichlorohydrin, and represented by the structural formula: $(C_{12}H_{22}O_{11})_m*(C_3H_5ClO)_n$. FICOLL PM400 was added to a bone marrow cell suspension at a final concentration of 1.9%, and the bone marrow cell suspension was subjected to the action of FICOLL PM400 for 20 minutes at room temperature.

FICOLL PM400 is a stable polymerized substance of sugar chain and has a molecular weight of about 400,000. FICOLL PM400 is not taken into cells, and it has not been reported that FICOLL PM400 activates cell surface receptors. Therefore, the present inventors suppose that the FICOLL PM400 has a mechanism of action such that the FICOLL PM400 interacts with a sugar chain structure on a cell surface, for example. Highly reproducible ischemic model mice developed by the present inventors (Taguchi et al. J Exp Stroke Transl Med. 2010; 3: 28-33) were used as ischemic models for verifying revascularization capability and vascular protection effect achieved by the bone marrow cells subjected to the action of FICOLL PM400. At 48 hours after induction of ischemia, $1\times10^5$ bone marrow cells subjected to the action of FICOLL PM400 were administered from a tail vain. At 24 hours after the cell administration, the revascularization effect in a surrounding area of an ischemic region and vascular protection effect at a central portion of the ischemic region were verified using an anti-CD31 antibody (Taguchi et al. J Clin Invest. 2004; 114(3): 330-8). Each group used in the experiment consisted of six ischemic mice.

The ischemic models for verifying the effect of the administration of bone marrow cells on microvessels were produced in the following manner. Eight week-old CB-17 mice were each subjected to general anesthesia using halothane anesthetic. Perforation was carried out from the left malar bone to directly reach the left middle cerebral artery, and an opening having a diameter of about 1.5 mm was formed in the skull base. The left middle cerebral artery was clotted at a point immediately behind the olfactory bundle (i.e., at a distal point relative to the cross portion of the olfactory bundle), using a bipolar electric cautery. After the clotting, the left middle cerebral artery was cut to be permanently occluded. In this manner, the ischemic models were produced which had high reproducibility of an ischemic region localized in the cortex of the left middle cerebral artery region and of the degree of ischemia.

The cells to be administered were treated in the following manner. A bone marrow fluid was taken from the femur and tibia of each mouse. Erythrocytes were precipitated using hydroxyethyl starch, thereby preparing a bone marrow cell suspension. FICOLL PM400 was added to the bone marrow cell suspension at a final concentration of 1.9%, and the bone marrow cell suspension was subjected to the action of FICOLL PM400 for 20 minutes at room temperature. Thereafter, in order to remove FICOLL PM400 from the cell suspension, PBS amounting to three times the volume of FICOLL PM400 was added. The cell suspension was then centrifuged (200 g×10 minutes), and a cell supernatant was removed. Following further addition of PSB, the cell suspension was subjected to centrifugation and supernatant removal. In this manner, a bone marrow cell suspension containing $1\times10^6$ bone marrow cells/ml was prepared. As untreated cells, a bone marrow cell suspension was kept at room temperature for 20 minutes, without addition of FICOLL PM400. Just like the cells subjected to the action of FICOLL PM400, this cell suspension was centrifuged twice. In this manner, a bone marrow cell suspension containing $1\times10^6$ bone marrow cells/ml was prepared.

The revascularization effect in a surrounding area of the ischemic region and the vascular protection effect at a central portion of the ischemic region achieved by the administration of the bone marrow cells were analyzed in the following manner. At 48 hours after the induction of ischemia, $1\times10^5$ bone marrow cells subjected to the action of FICOLL PM400 (FICOLL PM400-treated cells) or $1\times10^5$ bone marrow cells not subjected to the action of FICOLL PM400 (untreated cells) were administered from a tail vain. At 24 hours after the cell administration, perfusion fixation was performed using a paraformaldehyde fixative. Sections each having a thickness of 20 μm were prepared using a vibratome. According to a known method, microvessels were visualized using anti-CD31 antibody (Taguchi et al. J Clin Invest. 2004; 114: 330-338). The nuclei of the stained sections were stained with hematoxylin for clarifying the ischemic region. The revascularization effect in the surrounding area of the ischemic region and the vascular protection effect in the central portion of the ischemic region were analyzed.

Figure 1A:
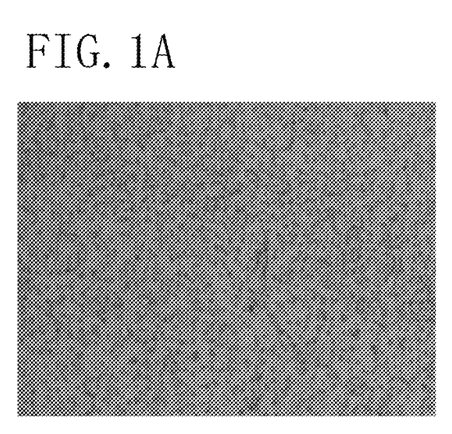
FIG. 1A shows a microvascular network of a normal mouse.
Figure 1B:
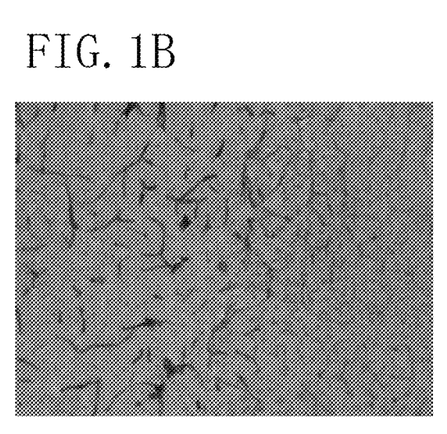
FIG. 1B shows a surrounding area of an ischemic region in a mouse to which bone marrow cells subjected to the action of a sugar chain polymer were administered.
Figure 1C:
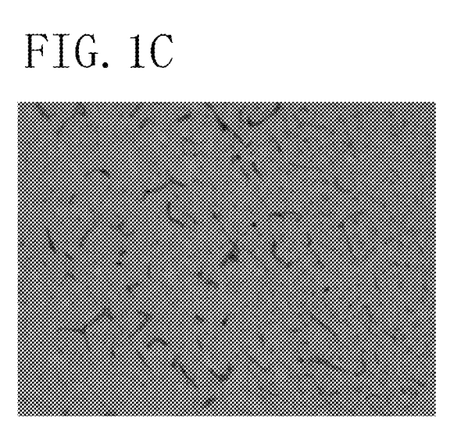
FIG. 1C shows a surrounding area of an ischemic region in a mouse to which bone marrow cells not subjected to the action of a sugar chain polymer were administered.

FIGS. 1A, 1B and 1C show the revascularization effect in the surrounding area of the ischemic region, achieved by the bone marrow cells subjected to the action of the sugar chain polymer (FICOLL PM400-treated cells). FIG. 1A shows a microvascular network in a normal mouse. FIG. 1B shows a microvascular network in a mouse to which the bone marrow cells subjected to the action of the sugar chain polymer were administered. As compared with FIG. 1A, FIG. 1B demonstrates an increased microvascular density in the surrounding area of the ischemic region. In contrast, as can be seen in FIG. 1C, a decrease in the microvascular density is observed in the surrounding area of the ischemic region in a mouse to which the bone marrow cells not subjected to the action of the sugar chain polymer (untreated cells). Each of FIG. 1A, FIG. 1B and FIG. 1C shows, in its right portion, an area in which distribution of hematoxylin-positive cell nuclei is dense. In this area, neuronal cells survived. On the other hand, an area in which distribution of hematoxylin-positive cell nuclei is thin represents an area in which neuronal cells were dead due to ischemia. The surrounding area of an ischemic region refers to an area near the boundary between the area with the dense distribution of the hematoxylin-positive cell nuclei and the area with the thin distribution of the hematoxylin-positive cell nuclei.

Figure 2A:
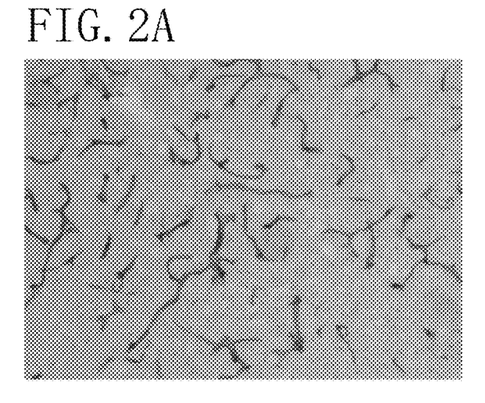
FIG. 2A shows a central portion of an ischemic region in a mouse to which bone marrow cells subjected to the action of a sugar chain polymer were administered.
Figure 2B:
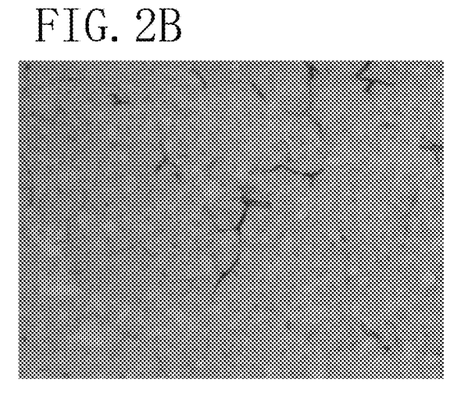
FIG. 2B shows a central portion of an ischemic region in a mouse to which bone marrow cells not subjected to the action of a sugar chain polymer were administered.

FIGS. 2A and 2B show, on a magnified view, vascular protection effect in the central portion of the ischemic region, achieved by the bone marrow cells subjected to the action of the sugar chain polymer. FIG. 2A shows that microvessels remained in the central portion of the ischemic region of a mouse to which the bone marrow cells subjected to the action of the sugar chain polymer (the FICOLL PM400-treated cells) were administered. On the other hand, FIG. 2B shows that microvascular networks were destroyed in a central portion of an ischemic region of a mouse to which the bone marrow cells not subjected to the action of the sugar chain polymer (untreated cells) were administered. Note that the distribution of hematoxylin-positive cell nuclei is thin in FIGS. 2A and 2B, which means that the neuronal cells were dead due to ischemia.

The results described above demonstrate that the bone marrow cells not subjected to the action of the sugar chain polymer (untreated cells) are ineffective in revascularization and vascular protection, whereas subjecting bone marrow cells to the action of the sugar chain polymer achieves revascularization and vascular protection effects.

Example 2

Ischemic damage suppression effect achieved by bone marrow cells subjected to the action of a sugar chain polymer FICOLL PM400 was added to a bone marrow cell suspension at a final concentration of 1.9%, and the bone marrow cell suspension was subjected to the action of FICOLL PM400 for 20 minutes at room temperature. Highly reproducible ischemic model mice developed by the present inventors (Taguchi et al. J Exp Stroke Transl Med. 2010; 3:28-33) were used as ischemic models for verifying ischemic damage suppression effect achieved by bone marrow cells subjected to the action of FICOLL PM400. At 48 hours after the induction of ischemia, $1 \times 10^5$ bone marrow cells subjected to the action of FICOLL PM400 were administered from a tail vain. At 30 days after the cell administration, the ischemic damage suppression effect was verified according to brain atrophy score of macro sample (Taguchi et al. Eur J Neurosci. 2007; 26(1): 126-33). The mice of an untreated control group were given the same amount (100 µm) of physiological saline as that given to the mice of the cell-administered group. The physiological saline was administered from a tail vain. Each group used in the experiment consisted of six ischemic mice. The ischemic models for verifying ischemic damage suppression effect achieved by the administration of bone marrow cells were produced in the same manner as in Example 1. The cells to be administered were treated in the same manner as in Example 1.

Figure 3:
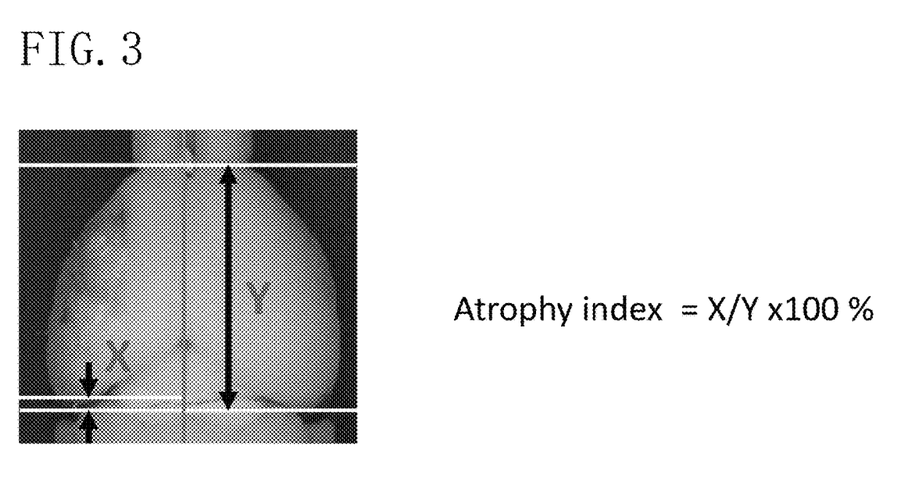
FIG. 3 shows how to measure Atrophy index.

The details of the ischemic damage score of macro sample are as follows. The cerebral ischemia models used in this study had ischemia localized in a region of cerebral cortex, which is perfused by the left middle cerebral artery. In this respect, after induction of ischemia, due to, for example, invasion by inflammatory cells, obvious atrophy appears in tissues in the ischemic region, as compared to the contralateral region (the region where no ischemia is induced). The present inventors have already presented that Atrophy index is useful for quantitative assessment of a degree of such atrophy (Taguchi et al. Eur J Neurosci. 2007; 26(1): 126-33). FIG. 3 shows how to measure the Atrophy index. As shown in FIG. 3, the Atrophy index is expressed by X/Y×100(%).

Figure 4:
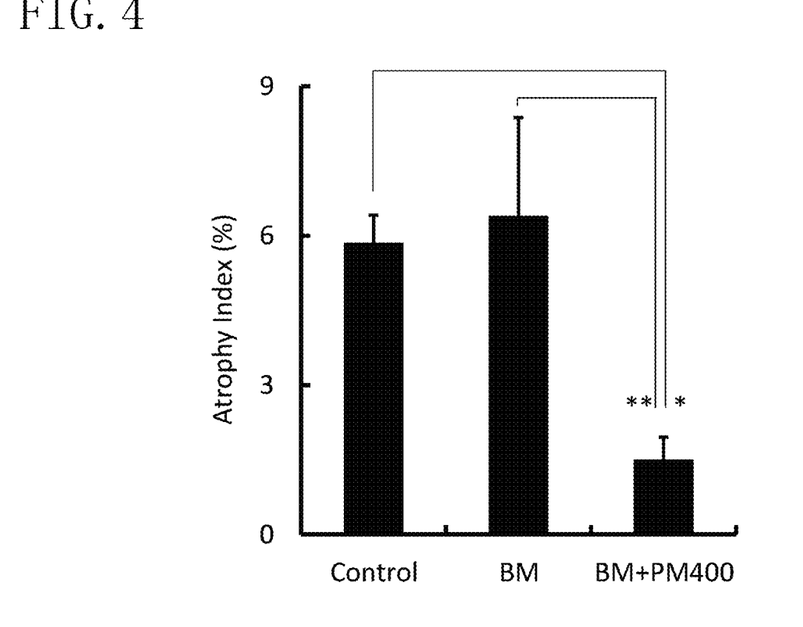
FIG. 4 shows therapeutic effect of reducing ischemic damage.

FIG. 4 shows the therapeutic effect of reducing ischemic damage. The Atrophy index is an index indicative of a degree of cerebral atrophy. "Control" represents the group to which physiological saline was administered. "BM" represents the group to which the untreated bone marrow cells (BM: Bone Marrow) not subjected the action of the sugar chain polymer were administered. "BM+FICOLL PM400" represents the group to which the bone marrow cells subjected to the action of the sugar chain polymer (FICOLL PM400) were administered. It was demonstrated that the administration of $1 \times 10^5$ bone marrow cells subjected to the action of the sugar chain polymer (FICOLL PM400-treated cells) achieves ischemic damage suppression effect of statistical significance, compared to the physiological saline-administered group. By contrast, for the administration of $1 \times 10^5$ bone marrow cells not subjected to the action of the sugar chain polymer (untreated cells), ischemic damage suppression effect was not observed. The mark "*" indicates a statistically significant difference between the Control group and the BM+FICOLL PM400 group, and the mark "**" indicates a statistically significant difference between the BM group and the BM+FICOLL PM400 group.

The results described above demonstrate that the bone marrow cells not subjected to the action of the sugar chain polymer (untreated cells) are ineffective in suppressing the ischemic damage, whereas subjecting bone marrow cells to the action of the sugar chain polymer achieves the effect of suppressing the ischemic damage.

Example 3

Effect of promoting functional recovery from ischemic damage, achieved by bone marrow cells subjected to the action of a sugar chain polymer FICOLL PM400 is a polymer produced by polymerizing sucrose which is a kind of saccharide. FICOLL PM400 was added to a bone marrow cell suspension at a final concentration of 1.9%, and the bone marrow cell suspension was subjected to the action of FICOLL PM400 for 20 minutes at room temperature. Highly reproducible ischemic model mice developed by the present inventors (Taguchi et al. J Exp Stroke Transl Med. 2010; 3: 28-33) were used as ischemic models for verifying effect of promoting functional recovery from ischemic damage, achieved by bone marrow cells subjected to the action of FICOLL PM400. At 48 hours after the induction of ischemia, $1 \times 10^5$ bone marrow cells subjected to the action of FICOLL PM400 were administered from a tail vain. At 30 days after the cell administration, the effect of promoting functional recovery from ischemic damage was verified with reference to the response to light-dark condition in an open-field test (Taguchi et al. J Clin Invest. 2004; 114: 330-8). Each group used in the experiment consisted of six ischemic mice. The ischemic models for verifying the effect of promoting functional recovery from ischemic damage achieved by the administration of the bone marrow cells were produced in the same manner as in Example 1. The cells to be administered were treated in the same manner as in Example 1.

As a method for assessing the effect of promoting functional recovery, the open-field test was conducted. The measurement principle and measurement method of the open-field test are as follows. A mouse is a nocturnal animal. It is known that a normal mouse moves less actively under lighted conditions and more actively in a dark environment. It has been reported that the cerebral cortex plays an important role in behavioral suppression under lighted conditions, and a cell treatment contributes to the recovery of the behavioral suppression function under lighted conditions (Taguchi et al. J Clin Invest. 2004; 114: 330-8). In this study, each mouse was put in an open-field measurement device (product of Kouiken Co., Ltd., with a free movement space of 40 cm×40 cm). The number of rearing was automatically counted for 30 minutes under lighted conditions, and thereafter, the number of rearing was counted for 30 minutes under dark conditions. The increase in motor activity shown when the lighted conditions were switched to the dark conditions was used as an index of functional recovery.

Figure 5:
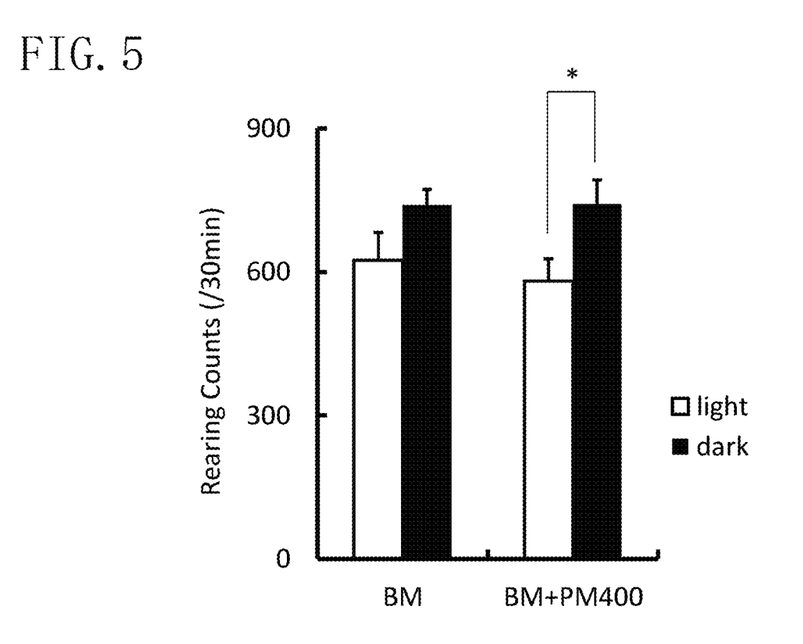
FIG. 5 shows results of improvement of functional recovery effect from ischemic damage, achieved by the administration of bone marrow cells.

FIG. 5 shows the results of functional recovery effect from ischemic damage achieved by the administration of bone marrow cells. "BM" represents the group to which the untreated bone marrow cells (BM: Bone Marrow) not subjected the action of the sugar chain polymer were administered. "BM+FICOLL PM400" represents the group to which the bone marrow cells subjected to the action of the sugar chain polymer (FICOLL PM400) were administered. FIG. 5 shows the rearing count of the group (BM Group) to which the untreated bone marrow cells not subjected the action of the sugar chain polymer were administered, and the rearing count of the group (BM+FICOLL PM400 Group) to which the bone marrow cells subjected to the action of the sugar chain polymer were administered. The white bars represent the rearing counts under the lighted conditions and the black bars represent the rearing counts under the dark conditions. Each mouse to which the untreated bone marrow cells not subjected the action of the sugar chain polymer were administered exhibited no significant increase in the motor activity in response to switching to the dark conditions. By contrast, it was observed that the administration of the bone marrow cells subjected to the action of the sugar chain polymer caused a statistically significant increase in motor activity in response to the dark conditions. The mark "*" indicates that in the BM+FICOLL PM400 Group, a statistically significant increase in the rearing count was confirmed in response to switching from the lighted conditions to the dark conditions. That is, it was demonstrated that the administration of the bone marrow cells subjected to the action of the sugar chain polymer is effective in improving the functional recovery of cranial nerves.

The results described above demonstrate that the administration of the bone marrow cells not subjected to the action of the sugar chain polymer (untreated cells) is ineffective in functional recovery from ischemic damage, whereas the administration of the bone marrow cells subjected to the action of the sugar chain polymer provides the effect of promoting functional recovery of cerebral cortex.

Example 4

Effect of promoting functional recovery from ischemic damage, achieved by bone marrow cells subjected to the action of maltose Maltose, which is a saccharide having a molecular weight of 342, was added to a bone marrow cell suspension at a final concentration of 10%, and the bone marrow cell suspension was subjected to the action of maltose for 20 minutes at room temperature. Highly reproducible ischemic model mice developed by the present inventors (Taguchi et al. J Exp Stroke Transl Med. 2010; 3: 28-33) were used as ischemia models for verifying effect of promoting functional recovery from ischemic damage, achieved by the bone marrow cells subjected to the action of maltose. At 48 hours after the induction of ischemia, $1 \times 10^5$ bone marrow cells subjected to the action of maltose were administered from a tail vain. At 30 days after the cell administration, the effect of promoting functional recovery from ischemic damage was verified with reference to the response to light-dark condition in an open-field test (Taguchi et al. J Clin Invest. 2004; 114: 330-8). Each group used in the experiment consisted of six ischemic mice. The ischemic models for verifying the effect of promoting functional recovery from ischemic damage achieved by the administration of the bone marrow cells were produced in the same manner as in Example 1. The cells to be administered were treated in the same manner as in Example 1, except that maltose was used instead of FICOLL PM400. The effect of promoting functional recovery was assessed in the same manner as in Example 3.

Figure 6:
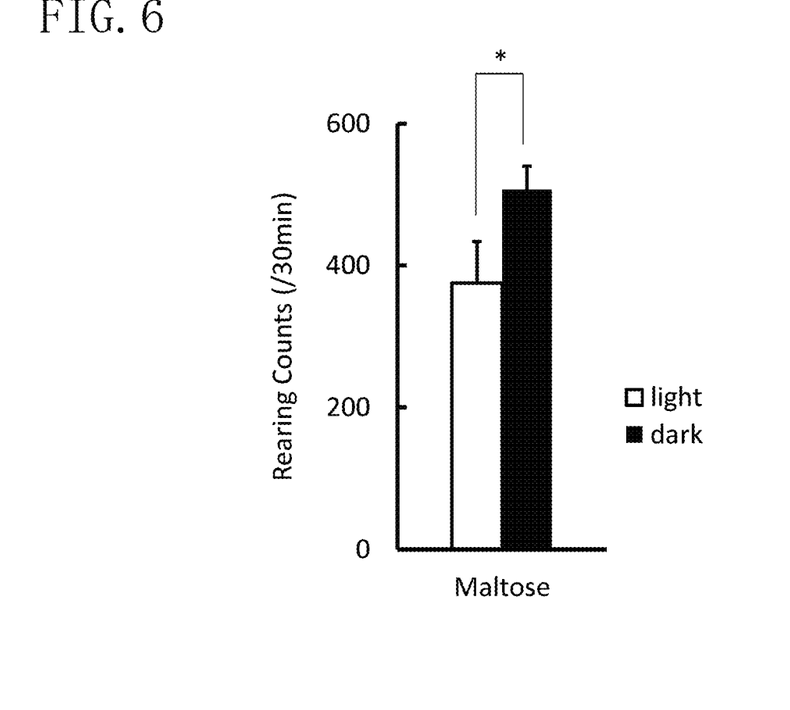
FIG. 6 shows results of improvement of functional recovery effect from ischemic damage, achieved by bone marrow cells subjected to the action of maltose.

FIG. 6 shows the effect of promoting functional recovery from ischemic damage, achieved by the bone marrow cells subjected to the action of maltose. The white bar represents the rearing count under the lighted conditions, and the black bar represents the rearing count under the dark conditions. The administration of $1 \times 10^5$ bone marrow cells subjected to the action of maltose caused statically significant recovery of motor suppression function under the lighted conditions. Thus, it was demonstrated that the cell administration is effective in promoting functional recovery of cerebral cortex. The mark "*" indicates that in the group to which the bone marrow cells subjected to the action of maltose, a statistically significant increase in the rearing count was confirmed in response to switching from the lighted conditions to the dark conditions.

Example 3 demonstrates that the untreated bone marrow cells are ineffective in functional recovery. This study demonstrates that subjecting bone marrow cells to the action of maltose makes the bone marrow cells effective in treatment, just like the FICOLL PM400-treated cells.

Example 5

Therapeutic effect on ischemic diseases, achieved by peripheral blood cells subjected to the action of a sugar chain polymer In order to demonstrate that the scope of the present invention is not limited to the blood cells derived from bone marrow cells and that the present invention provides an advantage different from a cell separation effect achieved by FICOLL-Paque (a mixture of sodium diatrizoate and FICOLL PM400) which is frequently used in cytapheresis, the preset inventors verified therapeutic effect of blood cells derived from peripheral blood on ischemic diseases.

Peripheral blood was drawn from each mouse and placed as a layer on FICOLL-Paque (product of GE Healthcare Bioscience). The resultant was centrifuged at a centrifugal force of 400 G for 40 minutes. Thereafter, a layer between an erythrocyte layer and a plasma layer (buffy coat layer) was prepared. As a cell group of the peripheral blood buffy coat layer, the cells contained in the buffy coat layer were washed with PBS and used in the experiment. As a FICOLL PM400-treated cell group, the cells contained in the buffy coat layer were washed with PBS, and FICOLL PM400 was added at a final concentration of 1.9%. The cells were then subjected to the action of FICOLL PM400 for 20 minutes at room temperature. Thereafter, the cells were washed with PBS, and used in the experiment. Highly reproducible ischemic model mice developed by the inventors (Taguchi et al. J Exp Stroke Transl Med. 2010; 3: 28-33) were used as ischemic models for verifying the therapeutic effect on ischemic diseases which is achieved by the administration of the cells derived from peripheral blood. At 48 hours after the induction of ischemia, $1 \times 10^5$ peripheral blood buffy coat layer cells or $1 \times 10^5$ FICOLL PM400-treated cells were administered from a tail vain. At 30 days after the cell administration, the therapeutic effect on ischemic diseases was assessed according to the brain atrophy score of macro sample (Taguchi et al. Eur J Neurosci. 2007; 26(1): 126-33). The mice of an untreated control group were given the same amount (100 μm) of physiological saline as that given to the mice of the cell-administered group. The physiological saline was administered from a tail vain. Each group used in the experiment consisted of six ischemic mice. The ischemic models for verifying the therapeutic effect on ischemic diseases achieved by the administration of the cells derived from peripheral blood were prepared in the same manner as in Example 1.

Figure 7:
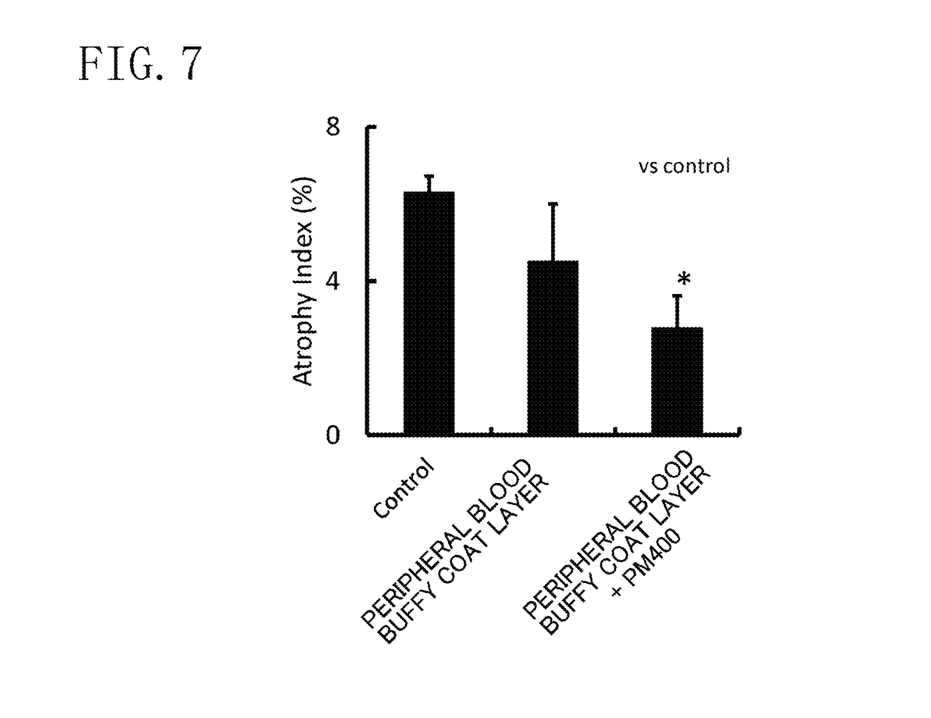
FIG. 7 shows a comparison between therapeutic effects on an ischemic disease, achieved by peripheral blood cells isolated using FICOLL-Paque, and by peripheral blood cells isolated using FICOLL-Paque and subjected to the action of FICOLL PM400.

The details of the ischemic damage score of macro sample are the same as in Example 2. FIG. 7 shows the therapeutic effect of reducing ischemic damage. The Atrophy index is an index indicative of a degree of cerebral atrophy. "Control" represents the group to which physiological saline was administered. "Peripheral blood buffy coat layer" represents the group to which the cells derived from the peripheral blood buffy coat layer prepared using the FICOLL-Paque were administered. "Peripheral blood buffy coat+FICOLL PM400" represents the group to which the cells that were derived from the peripheral blood buffy coat layer prepared using the FICOLL-Paque and that were subjected to the action of FICOLL PM400. The administration of the cell group of the peripheral blood buffy coat layer did not achieve statistically significant therapeutic effect, compared to the physiological saline-administered group. By contrast, it was demonstrated that the administration of the FICOLL PM400-treated cells achieved a statistically significant effect of reducing ischemic damage, compared to the physiological saline-administered group. The mark "*" indicates a statistically significant difference between the group to which the FICOLL PM400-treated cells were administered and the physiological saline-administered group.

The above described results demonstrate that treatment with FICOLL PM400 enables not only cells derived from bone marrow, but also cells derived from peripheral blood to achieve therapeutic effect on ischemic diseases, and that the present invention is capable of causing cells, which cannot achieve the therapeutic effect only by the cell isolation process using the FICOLL-Paque, to have the effect of treating ischemic diseases. Thus, it was demonstrated that the present invention achieves effects different from those provided by the cell isolation using the FICOLL-Paque and the process thereof.

Also in specific gravity centrifugation using the FICOLL-Paque, FICOLL PM400 which is a constituent of the FICOLL-Paque and the cells of the buffy coat layer may possibly be in contact with each other at the interface between the FICOLL-Paque layer and the buffy coat cell layer. Despite this possibility, the specific gravity centrifugation using the FICOLL-Paque did not allow the cells of the buffy coat layer derived from peripheral blood to achieve a function as a medicine for ischemic diseases. The present inventors attribute this to a combination of (i) and (ii) as follows: (i) To allow cells to achieve therapeutic effect, FICOLL PM400 and the blood cells need to be mixed sufficiently with each other. In the specific gravity centrifugation, a blood cell layer is placed on a FICOLL-Paque layer, and such placement does not at all cause the blood cell layer and the FICOLL-Paque layer containing FICOLL PM400 to be mixed with each other, and such contact limited to the interface therebetween is not enough to exhibit the effect of FICOLL PM400; and (ii) sodium diatrizoate existing in the FICOLL-Paque inhibits the effect of FICOLL PM400 on the blood cells. The present inventors attribute the mechanism, in which subjecting blood cells to the action of a sugar chain or a sugar chain structure disclosed herein allows hemocytes to achieve therapeutic effect on vascular damage, to modification of adhesion factor expressed on the surfaces of blood cells, in particular, to modification of blood cell sugar chain ligands (sugar chain structures including Sialyl-Lewis x) such as selectins (e.g., E-Selectin and P-Selectin) expressed on the endothelial cells of damaged blood vessels.

INDUSTRIAL APPLICABILITY

The present invention is useful for treatment and/or prevention of ischemic diseases.

What is claimed is:
1. A method for improving angiogenesis-promoting activity of blood cells or hemocytes, the method comprising: adding a copolymer of sucrose and epichlorohydrin to the blood cells or the hemocytes in a cell suspension; incubating the blood cells or the hemocytes with the copolymer of sucrose and epichlorohydrin for 5 minutes to 1 hour; and after incubating the blood cells and the hemocytes, separating the copolymer from the blood cells or the hemocytes using centrifugation.
2. The method of claim 1, wherein if the blood cells or the hemocytes are bone marrow cells, an erythrocyte fraction is removed but a leukocyte fraction is not removed.

* * * * *